United States Patent
Buschmann et al.

(10) Patent No.: US 6,828,345 B2
(45) Date of Patent: Dec. 7, 2004

(54) O-SUBSTITUTED 6-METHYLTRAMADOL DERIVATIVES

(75) Inventors: Helmut Buschmann, Aachen (DE); Babette-Yvonne Koegel, Langerwehe-Hamich (DE); Elmar Friderichs, Stolberg (DE); Dagmar Kaulartz, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 10/402,147

(22) Filed: Mar. 31, 2003

(65) Prior Publication Data

US 2003/0220389 A1 Nov. 27, 2003

Related U.S. Application Data

(63) Continuation of application No. PCT/EP01/11276, filed on Sep. 28, 2001.

(30) Foreign Application Priority Data

Sep. 29, 2000 (DE) .......................................... 100 49 483

(51) Int. Cl.$^7$ ...................... A61K 31/38; A61K 31/135; C07D 333/12; C07C 209/00
(52) U.S. Cl. ...................... 514/438; 514/646; 549/74; 564/445
(58) Field of Search ................................. 514/646, 438; 564/445; 549/74

(56) References Cited

U.S. PATENT DOCUMENTS

| | | | | |
|---|---|---|---|---|
| 3,652,589 | A | * 3/1972 | Flick et al. .................. | 548/578 |
| 4,155,935 | A | 5/1979 | Yardley et al. | |
| 5,728,885 | A | 3/1998 | Buschmann et al. | |
| 5,733,936 | A | * 3/1998 | Buschmann et al. ........ | 514/646 |
| 5,801,201 | A | 9/1998 | Graudums et al. | |
| 5,919,826 | A | * 7/1999 | Caruso ....................... | 514/629 |
| RE37,355 | E | * 9/2001 | Buschmann et al. ........ | 514/646 |
| 6,399,829 | B1 | * 6/2002 | Jarvi et al. .................. | 564/425 |
| 6,455,585 | B1 | * 9/2002 | Del Castillo Nieto et al. ................. | 514/533 |
| 6,469,213 | B1 | * 10/2002 | Schickaneder et al. ..... | 564/425 |
| 6,562,865 | B1 | * 5/2003 | Codd et al. ................. | 514/456 |
| 6,605,644 | B2 | * 8/2003 | Kamin et al. ............... | 514/646 |
| 6,642,275 | B2 | * 11/2003 | Alfonso et al. ............. | 514/646 |
| 6,649,783 | B2 | * 11/2003 | Kupper et al. .............. | 556/146 |

FOREIGN PATENT DOCUMENTS

| EP | 0 780 369 B1 | 12/1996 |
|---|---|---|
| EP | 0 786 450 B1 | 12/1996 |

* cited by examiner

*Primary Examiner*—Deborah C. Lambkin
(74) *Attorney, Agent, or Firm*—Crowell & Moring LLP

(57) ABSTRACT

The invention relates to O-substituted 6-methyl-tramadol derivatives, to methods for producing them, to medicaments containing these compounds, to the use of O-substituted 6-methyl-tramadol derivatives for producing medicaments for treating pain and other symptoms or diseases, and to methods of treatment using the medicaments.

8 Claims, No Drawings

O-SUBSTITUTED 6-METHYLTRAMADOL DERIVATIVES

CROSS REFERENCE TO RELATED APPLICATIONS

The present application is a continuation of International Patent Application No. PCT/EP01/11276, filed Sep. 28, 2001, designating the United States of America and published in German as WO 02/26694 A1, the entire disclosure of which is incorporated herein by reference. Priority is claimed based on Federal Republic of Germany Patent Application No. 100 49 483.8, filed Sep. 29, 2000.

BACKGROUND AND SUMMARY OF THE INVENTION

The present invention relates to O-substituted 6-methyltramadol derivatives, processes for their production, medicaments containing these compounds, and the use of O-substituted 6-methyltramadol derivatives for the production of medicaments for treating pain, and methods for treating pain using the medicaments.

The treatment of chronic and non-chronic pain conditions is very important in medicine. There is therefore a universal need for highly effective pain treatments. The urgent need for a patient-oriented and targeted treatment of chronic and non-chronic pain conditions, which is understood to include the successful and satisfactory treatment of pain on the part of the patient, is documented in the large number of scientific studies that have recently appeared in the field of applied analgesia and in basic research relating to nociception.

Conventional opioids such as morphine are highly effective in treating severe to extremely severe pain. Their use is however limited by the known side effects such as respiratory depression, vomiting, sedation, constipation and development of tolerance. Also, they are less effective in treating neuropathic or incidental pain afflicting in particular tumor patients.

DESCRIPTION OF THE INVENTION

An object on which the present invention is based was accordingly to provide new analgesically effective substances that are suitable for treating pain, in particular acute but also chronic and neuropathic pain.

The present invention accordingly provides O-substituted 6-methyltramadol derivatives of the general formula I

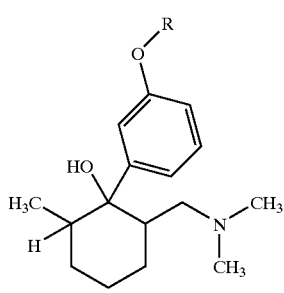

wherein

R is

H; $C_{1-3}$-alkyl that is saturated or unsaturated, branched or unbranched, unsubstituted or substituted; $CH_3$—$C_{4-6}$-cycloalkyl, $C_{4-6}$-cycloalkyl or thiophenyl;

optionally in the form of their racemates, their pure stereoisomers, in particular enantiomers or diastereomers, or in the form of mixtures of the stereoisomers, in particular of the enantiomers or diastereomers, in an arbitrary mixture ratio; in the prepared form or in the form of their acids or bases or in the form of their salts, in particular physiologically compatible salts, or in the form of their solvates, in particular the hydrates.

The substances according to the invention exhibit a pronounced analgesic action.

Within the context of the present invention alkyl radicals and cycloalkyl radicals are understood to be saturated and unsaturated (but not aromatic), branched, unbranched and cyclic hydrocarbons that may be unsubstituted or singly or multiply substituted. In this connection $C_{1-2}$-alkyl denotes $C_1$- or $C_2$-alkyl, $C_{1-3}$-alkyl denotes $C_1$-, $C_2$- or $C_3$-alkyl, $C_{1-4}$-alkyl denotes $C_1$-, $C_2$-, $C_3$- or $C_4$-alkyl, $C_{1-5}$-alkyl denotes $C_1$-, $C_2$-, $C_3$-, $C_4$ or $C_5$-alkyl $C_{1-6}$-alkyl denotes $C_1$-, $C_2$-, $C_3$-, $C_4$-, $C_5$- or $C_6$-alkyl, $C_{1-7}$-alkyl denotes $C_1$-, $C_2$-, $C_3$-, $C_4$-, $C_5$-, $C_6$- or $C_7$-alkyl, $C_{1-8}$-alkyl denotes $C_1$-, $C_2$-, $C_3$-, $C_4$-, $C_5$-, $C_6$-, $C_7$ or $C_8$-alkyl, $C_{1-10}$-alkyl, denotes $C_1$-, $C_2$-, $C_3$-, $C_4$-, $C_5$-, $C_6$-, $C_7$-, $C_8$-. $C_9$- or $C_{10}$-alkyl and $C_{1-8}$-alkyl denotes $C_1$-, $C_2$-, $C_3$-, $C_4$-, $C_5$-, $C_6$-, $C_7$-, $C_8$-. $C_9$-, $C_{10}$-, $C_{11}$-, $C_{12}$-, $C_{13}$-, $C_{14}$-, $C_{15}$-, $C_{16}$-, $C_{17}$- or $C_{18}$-alkyl. In addition $C_{3-4}$-cycloalkyl denotes $C_3$- or $C_4$-cycloalkyl, $C_{3-5}$-cycloalkyl denotes $C_3$-, $C_4$- or $C_5$-cycloalkyl, $C_{3-6}$-cycloalkyl denotes $C_3$-, $C_4$-, $C_5$- or $C_6$-cycloalkyl, $C_{3-7}$-cycloalkyl denotes $C_3$-, $C_4$-, $C_5$-, $C_6$- or $C_7$-cycloalkyl, $C_{3-8}$-cycloalkyl denotes $C_3$-, $C_4$-, $C_5$-, $C_6$-, $C_7$- or $C_8$-cycloalkyl, $C_{4-5}$-cycloalkyl denotes $C_4$- or $C_5$-cycloalkyl, $C_{4-6}$-cycloalkyl denotes $C_4$-, $C_5$- or $C_6$-cycloalkyl, $C_{4-7}$-cycloalkyl denotes $C_4$-, $C_5$-, $C_6$- or $C_7$-cycloalkyl, $C_{5-6}$-cycloalkyl denotes $C_5$- or $C_6$-cycloalkyl and $C_{5-7}$-cycloalkyl denotes $C_5$-, $C_6$- or $C_7$-cycloalkyl. The term cycloalkyl also includes singly or multiply, preferably singly, unsaturated cycloalkyls, as long as the cycloalkyl does not form an aromatic system. The alkyl or cycloalkyl radicals are preferably methyl, ethyl, vinyl (ethenyl), propyl, allyl(2-propenyl), 1-propinyl, methylethyl, butyl, 1-methylpropyl, 2-methylpropyl, 1,1-dimethylethyl, pentyl, 1,1-dimethylpropyl, 1,2-dimethylpropyl, 2,2-dimethylpropyl, hexyl, 1-methylpentyl, cyclopropyl, 2-methylcyclopropyl, cyclopropylmethyl, cyclobutyl, cyclopentyl, cyclopentylmethyl, cyclohexyl, cycloheptyl, cyclooctyl, but also $CHF_2$, $CF_3$, $CH_2OCH_3$ or $CH_2OH$.

In connection with alkyl and cycloalkyl the term "substituted" within the context of the present invention denotes—unless expressly defined otherwise—the substitution of at least one (optionally also several) hydrogen atom(s) by F, Cl, Br, I, $NH_2$, SH or OH, and the terms "multiply substituted" and "substituted" in the case of multiple substitution denote that the substitution takes place on different as well as on the same atoms multiply with the same or different substituents, for example triple substitution on the same C atom as in the case of $CF_3$, or at different positions as in the case of —CH(OH)—CH=CH—$CHCl_2$. Particularly preferred constituents in this connection are F, Cl and OH. With regard to cycloalkyl, the hydrogen atom may also be replaced by $OC_{1-3}$-alkyl or $C_{1-3}$-alkyl (in each case singly or multiply substituted or unsubstituted), in particular methyl, ethyl, n-propyl, i-propyl, $CF_3$ or ethoxy.

The term $(CH_2)_{3-6}$ is understood to denote —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, and the term $(CH_2)_{1-4}$ is understood to denote —$CH_2$—, —$CH_2$—$CH_2$—, —$CH_2$—$CH_2$—$CH_2$— and —$CH_2$—$CH_2$—$CH_2$—$CH_2$—etc.

The term "aryl radical" is understood to mean ring systems with at least one aromatic ring but without any heteroatom in any of the rings. Examples are phenyl, naphthyl, fluoranthenyl, fluorenyl, tetralinyl or indanyl, in particular 9H-fluorenyl or anthracenyl radicals, which may be unsubstituted or singly or multiply substituted.

The term "heteroaryl radical" is understood to mean heterocyclic ring systems with at least one unsaturated ring that may contain one or more heteroatoms, such as nitrogen, oxygen and/or sulfur, and which may also be singly or multiply substituted. Examples of the group of heteroaryls that may be mentioned include furan, benzofuran, thiophene, benzothiophene, pyrrole, pyridine, pyrimidine, pyrazine, quinoline, isoquinoline, phthalazine, benzo[1,2,5]thiadiazole, benzothiazole, indole, benzotriazole, benzodioxolane, benzodioxane, carbazole, indole and quinazoline.

In connection with aryl and heteroaryl, the term "substituted"—unless expressly stated otherwise—denotes the substitution of the aryl or heteroaryl by OH, F, Cl, Br, I, $NH_2$ $SH$, $CF_3$, $CH_2F$, $CHF_2$, CN, $NO_2$, $C_{1-6}$-alkyl (saturated), $C_{1-6}$-alkoxy or $C_{2-6}$-alkylene.

The term salt is understood to mean any form of the active constituent according to the invention which adopts an ionic form or is charged and is coupled to a counterion (a cation or an anion), and may be present in solution. The term is also understood to include complexes of the active constituent with other molecules and ions, in particular complexes that are complexed via ionic interactions. In particular the term is understood to mean physiologically compatible salts with cations or bases and physiologically compatible salts with anions or acids.

The term physiologically compatible salts with cations or bases is understood within the context of the present invention to mean salts of at least one of the compounds according to the invention—such as when deprotonated acid—as an anion, with at least one cation, preferably an inorganic cation, that are physiological compatible, especially when used in humans and/or other mammals. Particularly preferred are the salts of alkali and alkaline earth metals, but also with $NH_4^+$, and in particular mono- or di-sodium, mono- or di-potassium, magnesium or calcium salts.

The term physiologically compatible salt with anions or acids is understood within the context of the present invention to mean salts of at least one of the compounds according to the invention—such as when protonated, for example on the nitrogen atom—as a cation with at least one anion, especially a physiologically compatible anion, when used in humans and/or other mammals. In the context of the present invention the term is particularly understood to denote the salt formed with a physiologically compatible acid, namely salts with inorganic or organic acids that are physiologically compatible, especially when used in humans and/or other mammals. Examples of physiologically compatible acids include: hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salt is particularly preferred.

In a preferred embodiment of the invention, in the O-substituted 6-methyltramadol derivatives of formula I
R is
H; $C_{1-3}$-alkyl that is saturated or unsaturated, unbranched, unsubstituted or singly substituted, preferably with $OCH_3$; —$CH_3$—$C_{4-6}$-cycloalkyl or $C_{4-6}$-cycloalkyl that is saturated and unsubstituted; thiophenyl that is unsubstituted;
preferably R is
H, —$CH_3$, —$C_2H_5$, —$CH_2$—CH=$CH_2$, —$CH_2$—$CH_2$—O—$CH_3$, —C≡CH; cyclobutyl, cyclopentyl, —$CH_3$-cyclobutyl or thiophenyl, in each case unsubstituted;
in particular R is
H, —$CH_3$, —$C_2H_5$, —$CH_2$—CH=$CH_2$, —C≡CH; cyclobutyl, cyclopentyl or $CH_3$-cyclobutyl, in each case unsubstituted.

In a further preferred embodiment of the invention, in the O-substituted 6-methyltramadol derivatives of formula I, R is hydrogen.

In yet another preferred embodiment of the invention the O-substituted 6-methyltramadol derivatives are selected from the following group 2-dimethylaminomethyl-1-(3-methoxyphenyl)-6-methylcyclohexanol, 3-(2-dimethylaminomethyl-1-hydroxy-6-methylcyclohexyl)-phenol, 2-dimethylaminomethyl-1-(3-ethoxyphenyl)-6-methylcyclohexanol, 1-(3-allyloxyphenyl)-2-dimethylaminomethyl-6-methylcyclohexanol, 1-(3-cyclopentyloxyphenyl)-2-dimethylaminomethyl-6-methylcyclohexanol, 2-dimethylaminomethyl-1-[3-(2-methoxyethoxy)-phenyl]-6-methylcyclohexanol, 1-(3-cyclobutylmethoxyphenyl)-2-dimethylaminomethyl-6-methylcyclohexanol, 1-(3-cyclobutoxyphenyl)-2-dimethylaminomethyl-6-methylcyclohexanol, 2-dimethylaminomethyl-1-(3-ethynyloxyphenyl)-6-methylcyclohexanol, and 2-dimethylaminomethyl-6-methyl-1-[3-(thiophen-2-yloxy)-phenylcyclohexanol.

Preferably, the O-substituted 6methyltramadol derivative of formula I is selected from 2-dimethylaminomethyl-1-(3-methoxyphenyl)-6-methylcyclohexanol or 3-(2-dimethylaminomethyl-1-hydroxy-6-methylcyclohexyl)-phenol, and in particular is 3-(2-dimethylaminomethyl-1-hydroxy-6-methylcyclohexyl)-phenol.

The compound of formula I may be in the form of a racemate, a pure stereoisomer, in particular a pure enantiomer or diastereomer. The compound of formula I may also be in the form of mixtures of stereoisomers, in particular mixtures of enantiomers or diastereomers, in an arbitrary mixture ratio. The compound of formula I may be in the represented form, or in the form of an acid or base, or in the form of a salt, in particular a physiologically compatible salt, or in the form of a solvate, in particular a hydrate. Preferably, the compound of formula I is in the form of a hydrochloride, a bishydrochloride or a sodium salt.

In another preferred embodiment of the invention the O-substituted 6-methyltramadol derivatives according to the invention are present in a stereoisomeric form according to formula Ia:

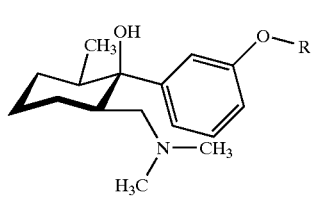

Ia

In yet another preferred embodiment of the invention the O-substituted 6-methyltramadol derivatives according to the invention are the (RS,RS,RS) racemate, the (-)-(S,S,S) or (+)-(R,R,R) enantiomer; or the (RS,SR,RS) racemate of 3-(2-dimethylaminomethyl-1-hydroxy-6-methylcyclohexyl)-phenol, preferably the (−)-(S,S,S) or (+)-(R,R,R) enantiomer of 3-(2-dimethylaminomethyl-1-hydroxy-6-methylcyclohexyl)-phenol, in particular the (−)-(S,S,S) enantiomer; or (−)-(1S,2S,6S)-3-(2-dimethylaminomethyl-1-hydroxy-6-methylcyclohexyl)-phenol, preferably in the form of a free base; or in the form of a salt, preferably a physiologically compatible salt, in particular the hydrochloride salt; or in the form of a solvate, in particular a hydrate.

The substances according to the invention are toxicologically harmless, and are suitable as a pharmaceutically active constituent in pharmaceutical compositions. The invention accordingly also provides medicaments containing at least one compound of formula I, as well as optionally suitable additives and auxiliary substances and/or optionally further active constituents.

The medicaments according to the invention may contain in addition to at least one O-substituted 6-methyltramadol derivative according to the invention, suitable additives and/or auxiliary substances, such as carrier materials, fillers, solvents, diluents, colorants and/or binders, and may be administered as liquid medicament forms in the form of injection solutions, droplets or juices, or as semi-solid medicament forms in the form of granules, tablets, pellets, patches, capsules, plasters or aerosols. The choice of the auxiliary substances, etc., as well as the amounts thereof to be used depend on whether the medicament is to be administered orally, perorally, parenterally, intravenously, intraperitoneally, intradermally, intramuscularly, intranasally, buccally, rectally or topically, for example to the skin, the mucous membranes or the eyes. For oral administration, preparations in the form of tablets, sugar-coated pills, capsules, granules, drops, juices and syrups are suitable, while for parenteral, topical and inhalative application, solutions, suspensions, readily reconstitutable dry preparations as well as sprays are suitable. O-substituted 6-methyltramadol derivatives according to the invention in a depôt form, in dissolved form or in a plaster, optionally with the addition of agents promoting skin penetration, are suitable percutaneous application preparations. Orally or percutaneously usable preparation forms may provide for a delayed release of the O-substituted 6-methyltramadol derivatives according to the invention. In principle further active constituents known to a person ordinarily skilled in the art may be added to the medicaments according to the invention.

The amount of active constituent to be administered to the patient varies depending on the patient's weight, type of application, medical indication for use and the severity of the condition. Normally 0.005 to 1000 mg/kg, preferably 0.05 to 5 mg/kg of at least one O-substituted 6-methyltramadol derivative according to the invention are applied.

The invention furthermore provides for the use of an O-substituted 6-methyltramadol derivative according to the invention for the production of a medicament for treating pain, in particular neuropathic, chronic or acute pain; or for treating migraine, hyperalgesia and allodynia, in particular thermal hyperalgesia, mechanical hyperalgesia and allodynia and cold-induced allodynia, or inflammatory or post-operative pain.

The invention additionally provides a process for treating a person or non-human mammal that requires treatment of medically relevant symptoms by administration of a therapeutically effective dose of an O-substituted 6-methyltramadol derivative according to the invention, or a medicament according to the invention. The invention relates in particular to suitable processes for treating pain, in particular neuropathic, chronic or acute pain, including migraine, hyperalgesia and allodynia, especially thermal hyperalgesia, mechanical hyperalgesia and allodynia and cold-induced allodynia, or for treating inflammatory or post-operative pain.

The invention moreover provides a process for preparing an O-substituted 6-methyltramadol derivative according to the invention as illustrated in the following description and examples. The present invention accordingly also provides a process for preparing an O-substituted 6-methyltramadol derivative according to the invention, in which 2-dimethylaminomethyl-6-methylcyclohexanone according to formula II is reacted with an organometallic compound of formula III

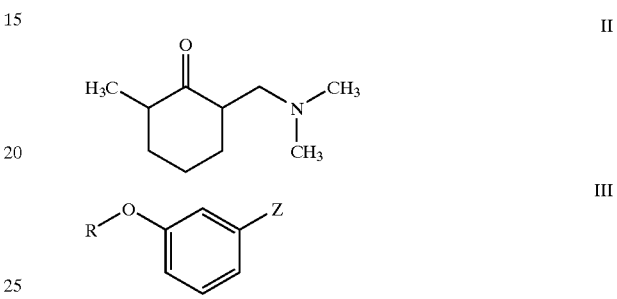

in which Z denotes Li and R has one of the meanings described above for formula I, to form a compound of formula I.

General Preparation of the Compounds According to the Invention

Reactions described in the literature (e.g., R. C. Larock, Comprehensive Organic Transformations, $2^{nd}$ Edition, Wiley, N.Y. 1999 and literature cited therein) as well as experimental procedures known to the ordinarily skilled person in the art were used for the syntheses.

O-derivatized 6-methyltramadol compounds of formula I can be prepared by a process which is characterized in that 2-dimethylaminomethyl-6-methylcyclohexanone II is reacted with an organometallic compound of formula III

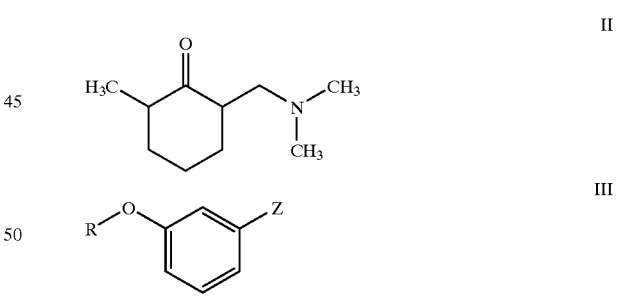

in which Z for compounds in which R≠H denotes MgCl, MgBr, MgI or Li, and for compounds in which R=H denotes Li, and R has one of the meanings given above for formula I, to form a compound of formula I.

Alternatively, the compounds of formula I can also be obtained by reacting 3-(2-dimethylaminomethyl-1-hydroxy-6-methylcyclohexyl)-phenol (formula IV) with a halogen compound of formula V, in which X denotes chlorine or bromine, with a base such as potassium tert.-butylate, sodium hydride, potassium carbonate, sodium carbonate, potassium hydrogen carbonate, or sodium hydrogen carbonate, in a solvent such as tetrahydrofuran or dimethylformamide at a temperature preferably between 0° C. and the reflux temperature of the solvent. The reaction may also be carried out using potassium hydroxide or sodium hydroxide in a solvent such as methanol or ethanol.

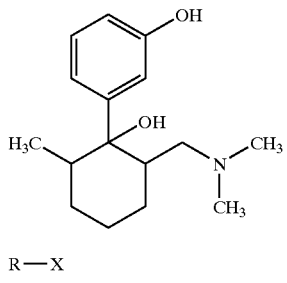

IV

R—X                V 3-(2-dimethylaminomethyl-1-hydroxy-6-methylcyclohexyl)-phenol of formula IV may also be obtained by reacting 2-dimethylaminomethyl-1-(3-methoxyphenyl)-6-methyl-cyclohexanol, (obtained by reacting 2-dimethylaminomethyl-6-methylcyclohexanone of formula II, with 3-bromoanisole and magnesium in a Grignard reaction), with a selective ether cleavage reagent such as diisobutylaluminium hydride, boron trichloride, boron tribromide or methionine.

The reaction with diisobutylaluminium hydride is preferably carried out in an aromatic hydrocarbon, for example toluene, at a temperature between 60° C. and 130° C. (Synthesis 1975, 617; DBP 2409990, 2409991, and Chem. Abstr. 84, 59862 (1974)).

In addition, 3-(2-dimethylaminomethyl-1-hydroxy-6-methyl-cyclohexyl)-phenol of formula IV can also be obtained from 1-(3-benzyloxyphenyl)-2-dimethylaminomethyl-6-methyl-cyclohexanol by reductive debenzylation. The debenzylation is carried out in the presence of platinum or palladium absorbed as catalyst on a support such as activated charcoal in the presence of hydrogen in a solvent such as acetic acid or a $C_{1-4}$-alkyl alcohol at pressures of 1 to 100 bar and temperatures of 20° to 100° C.

The reaction of dimethylaminomethyl-6-methylcyclohexanone II with a Grignard compound of formula III in which Z denotes MgCl, MgBr or MgI, or with an organolithium compound of formula III, in which Z denotes lithium, may be carried out in an aliphatic ether, for example diethyl ether, or tetrahydrofuran, or a mixture thereof, at temperatures between −70° C. and +60° C. Compounds of formula III in which Z denotes Cl, Br or I can be obtained by halogen-lithium exchange by reaction with for example an n-butyllithium/hexane solution.

Dimethylaminomethyl-6-methylcyclohexanone of formula II can be prepared by processes known in the literature (Houben-Weyl—Methoden der Organischen Chemie, E21b, 1995, pp. 1925–1929; M. Tramontini, L. Angiolini, Mannich Bases, Chemistry and Uses, CRS Press, 1994 and literature cited therein).

For example, dimethylaminomethyl-6-methylcyclohexanone of formula II can be obtained from 2-methylcyclohexanone by reaction with dimethylamine hydrochloride and formaldehyde in glacial acetic acid, water or in a $C_{1-4}$-alkyl alcohol, or by reaction with dimethylammonium methylene chloride in acetonitrile under acetyl chloride catalysis (Synthesis 1973, 703; Tietze, Eicher, Reaktionene und Synthesen im Organisch Chemischen Praktikum, Thieme Verlag, Stuttgart, 1991, p. 189).

The diastereomeric dimethylaminomethyl-6-methylcyclo-hexanones formed in the aminomethylation reaction can be obtained in a pure diastereomeric form either by column chromatography separation or by fractional crystallization of their hydrochlorides from an organic solvent such as 2-butanone or acetone. Separation is also possible via chiral columns and/or with chiral reagents, preferably tartaric acid or substituted tartaric acid.

Salt Formation

Compounds of formula I can be converted by a method well-known to one of ordinary skill in the art into their salts with physiologically compatible acids, for example hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, 1,1-dioxo-1,2-dihydrol$\lambda^6$-benzo[d]isothiazol-3-one (saccharinic acid), monomethylsebacic acid, 5-oxoproline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid , hippuric acid and/or aspartic acid. The salt formation is preferably carried out in a solvent, for example diethyl ether, diisopropyl ether, alkyl esters of acetic acid, acetone and/or 2-butanone or also water. For the production of the hydrochlorides, trimethylchlorosilane in aqueous solution is moreover suitable.

The invention is described in more detail hereinafter by means of examples, without however being restricted thereto.

EXAMPLES

The following examples illustrate compounds according to the invention as well as their preparation and investigations of their efficacy.

The following details apply in general:

The chemicals and solvents used were commercially obtained from customary suppliers (Acros, Avocado, Aldrich, Fluka, Lancaster, Maybridge, Merck, Sigma, TCI etc.) or were synthesized.

The analysis was carried out by ESI mass spectrometry and/or HPLC and/or NMR spectroscopy.

Examples 1–25

The compounds in the following list were prepared according to the general preparation procedure described above:

List of Examples:

| Ex. No. | R = | Stereo-isomerism | Name (without specifying stereoisomerism) |
|---|---|---|---|
| 1 | $CH_3$ | (RS,RS,RS) | 2-dimethylaminomethyl-1-(3-methoxyphenyl)-6-methylcyclohexanol |
| 2 | $C_2H_5$ | (RS,RS,RS) | 2-dimethylaminomethyl-1-(3-ethoxyphenyl)-6-methylcyclohexanol |
| 3 | H | (RS,RS,RS) | 3-(2-dimethylaminomethyl-1-hydroxy-6-methyl-cyclohexyl)phenol |
| 4 | —$CH_2$—CH=$CH_2$ (allyl) | (RS,RS,RS) | 1-(3-allyloxyphenyl)-2-dimethylaminomethyl-6-methylcyclohexanol |
| 5 | $CH_3$ | (−)-(S,S,S) | 2-dimethylaminomethyl-1-(3-methoxyphenyl)-6-methylcyclohexanol |
| 6 | $CH_3$ | (+)-(R,R,R) | 2-dimethylaminomethyl-1-(3-methoxyphenyl)-6-methylcyclohexanol |
| 7 | cyclopentyl | (RS,RS,RS) | 1-(3-cyclopentyloxyphenyl)-2-dimethylaminomethyl-6-methylcyclohexanol |

-continued

| Ex. No. | R = | Stereo-isomerism | Name (without specifying stereoisomerism) |
|---|---|---|---|
| 8 | H | (RS,SR,RS) | 3-(2-dimethylaminomethyl-1-hydroxy-6-methylcyclohexyl)-phenol |
| 9 | H | (−)-(S,S,S) | 3-(2-dimethylaminomethyl-1-hydroxy-6-methylcyclohexyl)-phenol |
| 10 | H | (+)-(R,R,R) | 3-(2-dimethylaminomethyl-1-hydroxy-6-methylcyclohexyl)-phenol |
| 11 | $C_2H_5$ | (−)-(S,S,S) | 2-dimethylaminomethyl-1-(3-ethoxyphenyl)-6-methylcyclohexanol |
| 12 | $C_2H_5$ | (+)-(R,R,R) | 2-dimethylaminomethyl-1-(3-ethoxyphenyl)-6-methylcyclohexanol |
| 13 | cyclopentyl | (−)-(S,S,S) | 1-(3-cyclopentyloxyphenyl)-2-dimethylaminomethyl-6-methylcyclohexanol |
| 14 | cyclopentyl | (+)-(R,R,R) | 1-(3-cyclopentyloxyphenyl)-2-dimethylaminomethyl-6-methylcyclohexanol |
| 15 | $CH_2CH_2$—O—$CH_3$ | (+)-(R,R,R) | 2-dimethylaminomethyl-1-[3-(2-methoxyethoxy)-phenyl]-6-methylcyclohexanol |
| 16 | methylene-cyclobutyl | (+)-(R,R,R) | 1-(3-cyclobutylmethoxyphenyl)-2-dimethylaminomethyl-6-methylcyclohexanol |
| 17 | methylene-cyclobutyl | (−)-(S,S,S) | 1-(3-cyclobutylmethoxyphenyl)-2-dimethylaminomethyl-6-methylcyclohexanol |
| 18 | $CH_2CH_2$—O—$CH_3$ | (−)-(S,S,S) | 2-dimethylaminomethyl-1-[3-(2-methoxyethoxy)-phenyl]-6-methylcyclohexanol |
| 19 | —C≡CH (alkinyl) | (+)-(R,R,R) | 2-dimethylaminomethyl-1-(3-ethynyloxyphenyl)-6-methylcyclohexanol |
| 20 | —C≡CH (alkinyl) | (−)-(S,S,S) | 2-dimethylaminomethyl-1-(3-ethynyloxyphenyl)-6-methylcyclohexanol |
| 21 | cyclobutyl | (+)-(R,R,R) | 1-(3-cyclobutoxyphenyl)-2-dimethylaminomethyl-6-methylcyclohexanol |
| 22 | cyclobutyl | (−)-(S,S,S) | 1-(3-cyclobutoxyphenyl)-2-dimethylaminomethyl-6-methylcyclohexanol |
| 23 | 2-thienyl | (RS,RS,RS) | 2-dimethylaminomethyl-6-methyl-1-[3-(thiophen-2-yloxy)-phenyl]-cyclohexanol |
| 24 | 2-thienyl | (+)-(R,R,R) | 2-dimethylaminomethyl-6-methyl-1-[3-(thiophen-2-yloxy)-phenyl]-cyclohexanol |
| 25 | 2-thienyl | (−)-(S,S,S) | 2-dimethylaminomethyl-6-methyl-1-[3-(thiophen-2-yloxy)-phenyl]-cyclohexanol |

Example 26

Preparation of (−)-(1S,2S,6S)-3-(dimethylaminomethyl-1-hydroxy-6-methylcyclohexyl)-phenol, hydrochloride according to Scheme 1

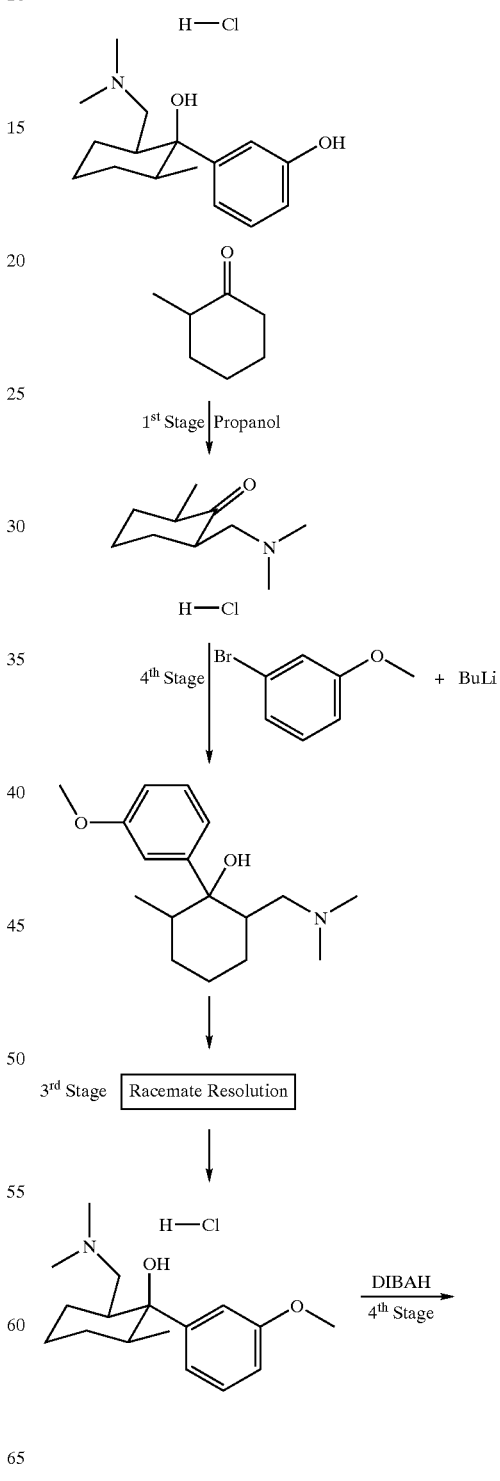

-continued

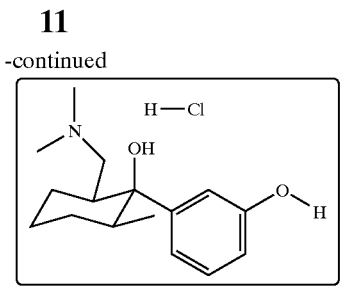

-continued

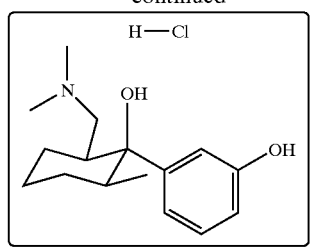

Example 27

Preparation of (−)-(1S,2S,6S)-3-(2-dimethylaminomethyl-1-hydroxy-6-methylcyclohexyl)-phenol, hydrochloride according to Scheme 2

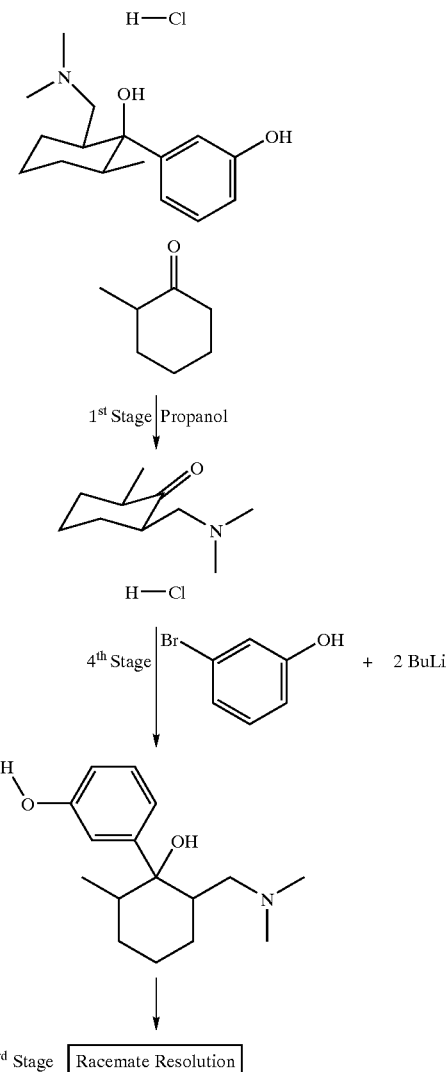

Example 28

Preparation of (−)-(1S,2S,6S)-3-(2-dimethylaminomethyl-1-hydroxy-6-methylcyclohexyl)-phenol, hydrochloride by the following process

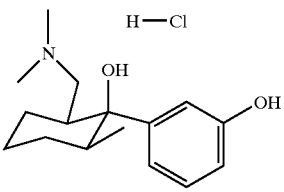

1st Stage (2RS,6RS)-2-dimethylaminomethyl-6-methylcyclohexanone, hydrochloride Reaction Equation:

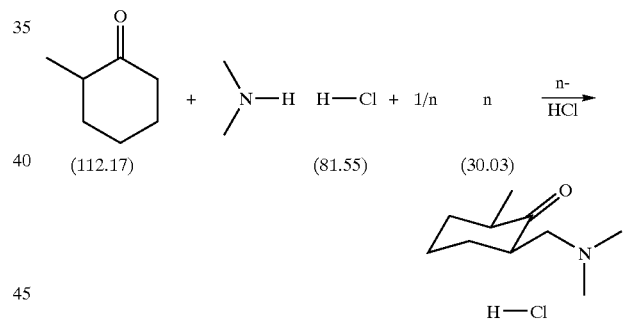

Reactants:
  363 ml=335.4 g=3.00 mole 2-methylcyclohexanone
  108 g=3.60 mole paraformaldehyde (1.2 equivalents)
  245 g=3.00 mole dimethylamine hydrochloride (1 equivalent)
  1.0 ml conc. $H_2SO_4$
  500 ml n-propanol Procedure:

2-methylcyclohexanone, dimethylamine hydrochloride and paraformaldehyde were suspended in 500 ml of n-propanol, and 1.0 ml of conc. sulfuric acid was added. The reaction mixture was then heated for 2 hours under reflux. After ca. 30 minutes a clear solution had formed (reaction check by thin layer chromatography; solvent: ethyl acetate/methanol=1:1; sample preparation: 20 μl reaction mixture +980 μl ethanol, 1 μl of each applied). It should be noted however that on heating at ca. 80° C. internal temperature, an exothermic reaction is observed.

The solvent was removed by distillation on a rotary evaporator (60° C. bath temperature, 100–40 Torr).

The residue was dissolved in 1500 ml of acetone, and 75 ml of water were added. The suspension was stirred for 1 hour at 60° C. and allowed to stand overnight at room temperature. The residue was suction filtered and then washed with acetone (twice with 100 ml). After drying in vacuo, 231 g of Mannich hydrochloride were isolated.

Yield: 231 g (37% of theory)

(2RS)-2-dimethylaminomethyl-2-methylcyclohexanone hydrochloride is formed as main product. The diastereomeric 6-methyl compound with axial methyl group is not formed. In addition, the mother liquor contains minor amounts of bis-Mannich condensation products.

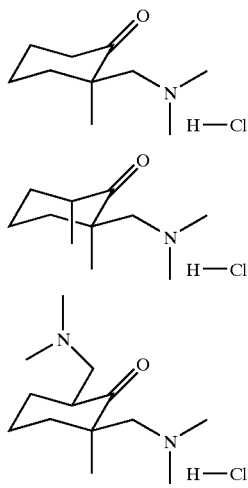

Characterization:

| Description: | White crystalline substance, free from visible impurities |
|---|---|
| Phys. properties: | Melting point: 164–165° C. |
| Investigation methods: | a) GC: AC/GC, Report No. IL 3121–IL 3122 CP 9000 dual system Channel 0: 25 m Fs. SE 54-CB-1 $^v$dlt = 250° C. isothermal $^v$inj = 230° C. $^v$oven = 130° C. Carrier: helium: 100 KPa Range 2 Amount of sample used: 1 µl organic phase; Sample preparation: 20 mg substance + 2 drops 5 N NaOH + 200 µl ethyl acetate. |
|  | b) TLC: with concentration zone (Merck) Solvent: ethyl acetate:methanol = 1:1; Detection: iodine chamber, UV lamp |
| Purity: | TLC: one main spot, >99% GC: >98% |
| Identity: | $^1$H-NMR, $^{13}$C-NMR correspond |

2$^{nd}$ Stage (1RS,2RS,6RS)-3-(2-dimethylaminomethyl-1-hydroxy-6-methylcyclohexyl)-phenol, hydrochloride Reaction Equation:

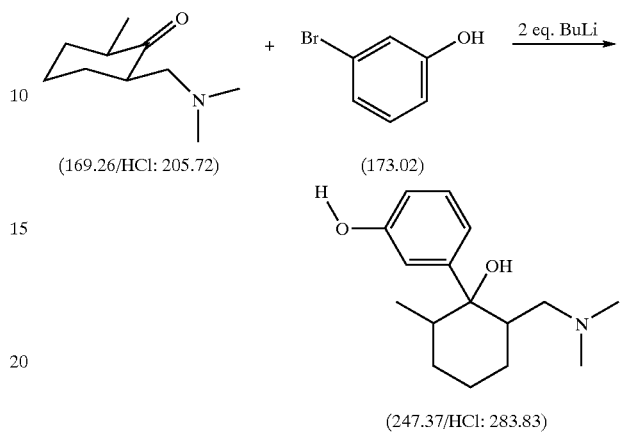

Reactants:
17.3 g=100 mmole 3-bromophenol
125 ml 1.6 molar n-butyllithium solution in hexane=200 mmole
16.9 g=100 mmole (2RS,6RS)-2-dimethylaminomethyl-6-methylcyclohexanone (base from Stage 1)

Procedure:

17.3 (=100 mmole) of 3-bromophenol were dissolved in 80 ml of dry tetrahydrofuran and cooled to −20° C. After addition of 125 ml (200 mmole) of 1.6 molar n-butyllithium solution in hexane, the reaction mixture was stirred for 2 hours at −25° C. 16.9 g (100 mmole) of (2RS,6RS)-2-dimethylamino-methyl-6-methylcyclohexanone (base from Stage 1) dissolved in 50 ml of dry tetrahydrofuran were then added dropwise at −25° C. The reaction mixture was heated to room temperature within 2.5 hours.

The reaction mixture was worked up by adding 100 ml of 5% hydrochloric acid dropwise while cooling in an ice bath so that the internal temperature did not rise above 15° C. After separation of the phases the aqueous phase was extracted three times with 50 ml of ether. The aqueous phase was made alkaline with concentrated sodium hydroxide and re-extracted with ether in order to separate the n-butyl addition product and unreacted Mannich base. After careful neutralization with hydrochloric acid the aqueous phase was re-acidified and then, in order to isolate the pheol, was made alkaline with sodium carbonate followed by extraction with ethyl acetate. After removing the solvent by distillation the residue (25 g) was dissolved in 250 ml of acetone and conc. hydrochloric acid was added. 12.48 g of hydrochloride crystallized out at 4–5° C.

Yield: 12.48 g (44% of Theory)

Characterization:

| Description: | White crystalline substance, free from visible impurities |
|---|---|
| Phys. properties: | Melting point: ° C. |
| Investigation methods: | TLC: HPTLC with concentration zone (Merck) Solvent: ethyl acetate:methanol = 1:1 Methylene chloride:methanol:glacial acetic acid = 10:1:1 Detection: iodine chamber, UV lamp (254 nm) |

| | |
|---|---|
| Purity: | TLC: one main spot, >99% |
| Identity: | $^1$H-NMR, $^{13}$C-NMR correspond |

3$^{rd}$ Stage
Racemate Resolution (−)-(1S,2S,6S)-3-(2-dimethylaminomethyl-1-hydroxy-6-methylcyclohexyl)-phenol, hydrochloride Racemate (−)-Enantiomer (+)-Enantiomer Reaction Equation:

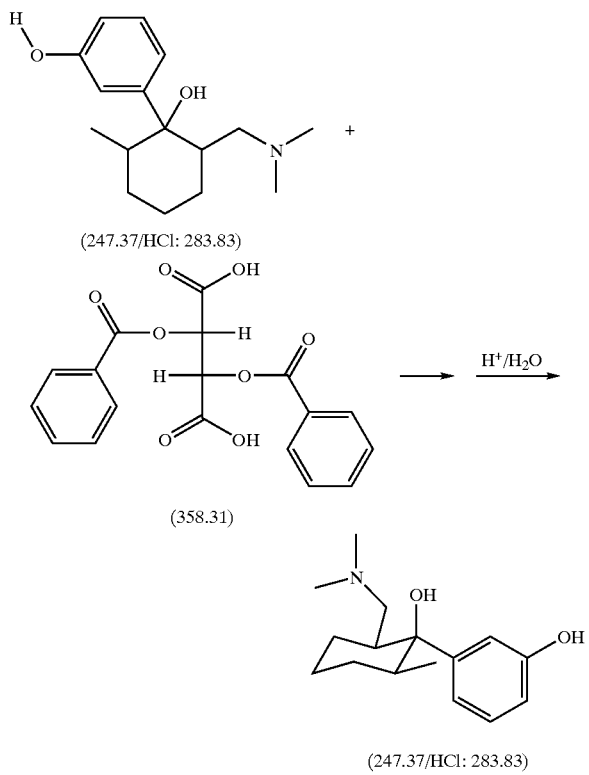

(247.37/HCl: 283.83)

(358.31)

(247.37/HCl: 283.83)

Procedure:

2-butanone
a) Precipitation with (+)-di-O,O'-p-toluyltartaric acid
Reactants:

24.7 g=100 mmole (1RS,2RS,6RS)-3-(2-dimethylaminomethyl-1-hydroxy-6-methylcyclohexyl)-phenol (racemic base from Stage 2)

35.8 g=100 mmole (+)-di-O,O'-p-benzoyl-tartaric acid

The base was freed from (1RS,2S,6RS)-3-(2-dimethylamino-methyl-1-hydroxy-6-methylcyclohexyl)-phenol hydrochloride (Stage 2) with dichloromethane/concentrated sodium carbonate solution. After drying the solution the dichloromethane was distilled off in vacuo. 24.7 g of the racemate were dissolved in 20 ml of 2-butanone and a solution of 35.8 g of (+)-di-O,O'-p-benzoyltartaric acid in 400 ml of 2-butanone was added while stirring. After seeding, the crystallization of the tartaric acid salt began. The reaction mixture was allowed to stand overnight at room temperature. The crystal mash was suction filtered and washed with precooled 2-butanone (2×50 ml). 25.4 g of tartaric acid salt were obtained after drying in vacuo. Removal of the solvent from the mother liquor by distillation yielded 37 g of a syrupy residue.

Yield: 25.4 g dibenzoyltartaric acid salt 37.0 g residue from the mother liquor b) Release of the Bases and Recovery of the (+)-di-O,O'-p-benzoyltartaric acid The dibenzoyltartaric acid salt (25 g) was dissolved in 100 ml of water and 5 ml of conc. hydrochloric acid were added. To remove the (+)-di-O,O'-p-benzoyltartaric acid, the aqueous phase was extracted with ether (2×50 ml) To free the base 35 ml of conc. sodium hydrogen carbonate solution were added and extraction was performed with dichloromethane (2×100 ml). After drying the organic phase over sodium sulfate and removing the solvent by distillation, 9.8 g of base were obtained with an enantiomer excess of >98% (HPLC).

To free the base from the mother liquor, the latter was dissolved in 150 ml of water, and 8 ml of conc. hydrochloric acid were added. To remove the (+)-di-O,O'-p-benzoyltartaric acid the aqueous phase was similarly extracted with ether (2×50 ml) and then made alkaline with 57 ml of concentrated sodium carbonate solution. Extraction with dichloromethane yielded 14.5 g of base.

The combined ether phases were dried over sodium sulfate. After removing the solvent by distillation and drying in vacuo (50° C. bath temperature at 10–20 Torr), 35 g of (+)-di-O,O'-p-benzoyltartaric acid were recovered.

Yield: 9.8 g base from tartaric acid salt (ee>98%)

77 g base from mother liquor (ee=66%)

35 g (+)-di-O,O'-p-benzoyltartaric acid recovered

Characterization:

| | |
|---|---|
| Description: | White crystalline substance, free from visible impurities |
| Phys. properties: | Melting point: 237–239° C. |
| | $[\alpha]_D^{RT} = -36.4°$ (c = 1.01; methanol) |
| Investigation methods: | a) HPLC; |
| | Chiracel OD (with 250 × 4.6 mm preliminary column), LKB pump |
| | Solvent: hexane:isopropanol:diethylamine = 990:10:1 |
| | Sample amount added: 20 μl (0.1% in eluent) 0.75 ml/min |
| | UV 273 nm, R.: 0.16 |
| | b) TLC: HPTLC with concentration zone (Merck) |
| | Solvent: ethyl acetate:methanol = 1:1 |
| | Methylene chloride:methanol:glacial acetic acid = 10:1:1 |
| | Detection: iodine chamber: UV lamp |
| Purity: | TLC: one main spot, >99% |
| | HPLC: >99% |
| Optical purity: | HPLC: ee >99.5 |
| | (−)-enantiomer:(+)-enantiomer 99.75:0.25 |
| Identity: | $^1$H-NMR, $^{13}$C-NMR, IR, UV correspond |

Pharmacological Investigations

Example 29
Writhing Test in Mice

The analgesic effectiveness of the compounds according to the invention was investigated in mice using the phenylquinone-induced writhing test as modified by I. C. Hendershot, J. Forsaith in J. Pharmacol. Exptl. Ther. 125, 237 (1959). Male NMRI mice weighing between 25 and 30 g were used for this purpose. Groups of 10 animals per substance dose received intraperitoneally 30 minutes after oral administration of a compound according to the invention, 0.3 ml per mouse of a 0.02% aqueous phenylquinone solution (phenylbenzoquinone, from Sigma, Deisenhofen; solution prepared by addition of 5% ethanol and storage in a water bath at 45° C.). The animals were then placed individually in observation cages. The number of pain-induced stretching movements (writhing reaction= contortion of the body accompanied by stretching of the rear extremities) was counted using a push-button counter 5–20 minutes after administration of the phenylquinone. The $ED_{50}$ values (effective dose with 50% inhibition of the writhing reaction) were calculated with 95% level of confidence by means of regression analysis (evaluation program from Martens EDV-Service, Ekental) from the dose-dependent reduction in the writhing reaction compared to mice investigated in parallel to which only phenylquinone had been administered. All investigated compounds according to the invention exhibited an excellent analgesic action. The results are summarized in Table I.

TABLE I

Writhing Inhibition Tests

| Example No. | ED50 [mg/kg orally] |
|---|---|
| 3 | 2.09 |
| 4 | 9.38 |
| 5 | 11.0 |
| 6 | 6.58 |
| 8 | 14.0 |
| 9 | 19.8 |
| 10 | 5.3 |
| 11 | 21.6 |
| 12 | 4.39 |
| 14 | 26.2 |
| 16 | 32.8 |

Example 30
Analgesia Investigation in the Tail-flick Test on Mice

The analgesic effectiveness of the compounds according to the invention was investigated by the focussed beam (tail-flick) test in mice according to the method developed by D'Amour and Smith (J. Pharmaceutical. Exp. Ther. 72, 74 79 (1941)). NMR mice weighing between 20 and 24 g were used for this purpose. The animals were placed individually in special test cages and the base of the tail was subjected to a focused beam of light from an electric lamp (tail-flick type 55/12/10.fl, Labtec, Dr Hess). The lamp intensity was adjusted so that the time from when the lamp was switched on to the sudden withdrawal of the tail (pain latency) was 3 to 5 seconds in the case of untreated animals. Before administration of a compound according to the invention the animals were pre-tested twice within 5 minutes and the mean value of these measurements was calculated as a pre-test mean value. The pain measurements were carried out 20, 40 and 60 minutes after intravenous administration. The analgesic action was calculated as the increase in the pain latency (% MPE) according to the following formula:

$$[(T_1-T_0)/(T_2-T_0)] \times 100$$

Here $T_0$ is the latency time before application of the substance and $T_1$ the latency time after application of the substance, and $T_2$ is the maximum exposure time (12 sec).

In order to determine the dose dependence the respective compound according to the invention was applied in 3 to 5 logarithmically increasing doses that included in each case the threshold dose and the maximal effect dose, and the $ED_{50}$ values were determined by means of regression analysis. The $ED_{50}$ calculation was carried out at the effect maximum 20 minutes after intravenous administration of the substance.

The investigated compounds according to the invention exhibited an excellent analgesic effect. The results are summarized in Table II.

TABLE II

Tail-flick Tests

| Example No. | $ED_{50}$ [mg/kg i.v.] |
|---|---|
| 1 | 5.6 |
| 2 | 11.9 |
| 3 | 2.15 |
| 4 | 20.2 |
| 5 | 42.9 (orally) |
| 6 | 7.73 |
| 9 | 14.7 |
| 10 | 0.91 |
| 12 | 13.45 |
| 14 | 20.0 |
| 16 | 21.5 |
| 19 | 14.7 |
| 21 | 30.0 |

What is claimed is:

1. A compound corresponding to formula 1a, which is in an isolated stereoisomeric form:

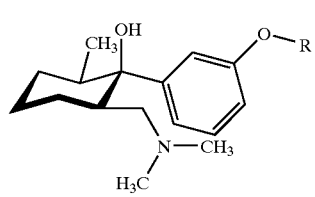

Ia wherein R is H; $C_{1-3}$-alkyl that is saturated or unsaturated, branched or unbranched, unsubstituted or substituted; $CH_3-C_{4-6}$-cycloalkyl: $C_{4-6}$-cycloalkyl or thiophenyl, or a derivative thereof in the form of a salt, a base, an acid or a solvate.

2. A compound according to claim 1, wherein the compound is a (−)-(S,S,S) or a (+)-(R,R,R) enantiomer.

3. A compound according to claim 1, wherein the compound is a (−)-(S,S,S) or (+)-(R,R,R) enantiomer of 3-(2-dimethylaminomethyl-1-hydroxy-6-methylcyclohexyl)-phenol.

4. A compound according to claim 3, wherein the compound is a (−)-(S,S,S) enantiomer.

5. A compound according to claim 1, wherein the compound is (−)-(1S,2S,6S)-3-(2-dimethylaminomethyl-1-hydroxy-6-methylcyclohexyl)-phenol.

6. A pharmaceutical composition comprising at least one compound or a derivative thereof according to claim 1, and a pharmaceutically acceptable exicipient.

7. A method for the treatment of pain, migraine, hyperalgesia and allodynia, comprising administering an effective amount of the pharmaceutical composition of claim 6 to a patient in need thereof.

8. A method according to claim 7, wherein the method is for the treatment of neuropathic, chronic or acute pain; thermal hyperalgesia, mechanical hyperalgesia, allodynia or cold-induced allodynia; or inflammatory or post-operative pain.

* * * * *